United States Patent [19]
Diesen et al.

[11] Patent Number: 5,196,621
[45] Date of Patent: Mar. 23, 1993

[54] PROCESS FOR THE CYCLODIMERIZATION OF 1,3-BUTADIENES TO 4-VINYLCYCLOHEXENES

[75] Inventors: Ronald W. Diesen; Kenneth A. Burdett; Ravi S. Dixit; Stanley S. T. King; Michael M. Olken, all of Midland, Mich.

[73] Assignee: The Dow Chemical Company, Midland, Mich.

[21] Appl. No.: 688,808

[22] Filed: Apr. 19, 1991

[51] Int. Cl.⁵ ............................................. C07C 2/50
[52] U.S. Cl. .................................. 585/361; 585/510; 585/530; 585/533; 585/366
[58] Field of Search ................ 585/361, 520, 530

[56] References Cited

U.S. PATENT DOCUMENTS

| | | | |
|---|---|---|---|
| 3,013,982 | 12/1961 | Breck et al. | 252/455 |
| 3,013,985 | 12/1961 | Breck et al. | 252/455 |
| 3,200,082 | 8/1965 | Breck et al. | 252/455 |
| 3,444,253 | 5/1969 | Remlinger et al. | 585/366 |
| 3,497,462 | 2/1970 | Kruerke | 252/454 |
| 3,755,540 | 8/1973 | Rosback | 423/328 |
| 3,929,621 | 12/1975 | Lussier et al. | 208/120 |
| 4,125,483 | 11/1978 | Downing et al. | 252/455 R |
| 4,126,643 | 2/1978 | Paxson et al. | 585/417 |
| 4,278,650 | 7/1981 | Dorrance | 423/579 |
| 4,348,272 | 9/1982 | Tu | 208/111 |
| 4,500,646 | 2/1984 | Denise et al. | 502/78 |
| 4,665,247 | 5/1987 | Dessau | 585/361 |
| 4,783,433 | 11/1988 | Tajima et al. | 502/74 |
| 4,814,527 | 3/1989 | Diesen | 570/243 |

FOREIGN PATENT DOCUMENTS 0261730 3/1988 European Pat. Off. .
1488521 10/1977 United Kingdom .
1554942 10/1979 United Kingdom .

OTHER PUBLICATIONS

Maxwell et al: Journal of Catalysis, 41, 412-419, 1976 "A Kinetic Study of the Reduction of Divalent Copper-Exchanged Faujasite with Butadiene and Ammonia".
P. Renger, F. Janowski, F. Wolf and E. Jahn, Z. Chem., 19(5), (1979) 194-195. (Translation enc.).
I. E. Maxwell, R. S. Downing, and S. A. J. Van Langen, Journal of Catalysis, 61, (1980) 485-492.
H. Reimlinger, U. Kruerke, and E de Ruiter, Chem. Ber., 103, (1970) 2317-2319. (Translation Enclosed).
I. E. Maxwell, J. J. de Boer and R. S. Downing, Journal of Catalysis, 61, (1980) 493-502.

Primary Examiner—Asok Pal
Assistant Examiner—P. Achutamurthy
Attorney, Agent, or Firm—Marie F. Zuckerman

[57] ABSTRACT

A process for the cyclodimerization of 1,3-butadienes to 4-vinylcyclohexenes comprising contacting a butadiene in the presence of a promoting amount of a hydroxylic solvent with a catalyst containing copper(I) ions supported on a carrier. A second process for the cyclodimerization of 1,3-butadienes to 4-vinylcyclohexenes comprising contacting a butadiene with a catalytic amount of a copper(I)-impregnated aluminosilicate zeolite characterized by a bulk $SiO_2/Al_2O_3$ molar ratio in the range from about 5 to about 50 and a framework $SiO_2/Al_2O_3$ molar ratio of at least about 15. A catalyst composition comprising a copper(I)-impregnated zeolite of specified bulk and framework silica to alumina molar ratios and specified water content. The catalyst exhibits high activity and long lifetime in the aforementioned dimerization processes and is easily regenerated.

55 Claims, 3 Drawing Sheets

"k vs Wt % Water"

PROCESS FOR THE CYCLODIMERIZATION OF 1,3-BUTADIENES TO 4-VINYLCYCLOHEXENES

BACKGROUND OF THE INVENTION

This invention pertains to a process for the cyclodimerization of 1,3-butadiene or substituted 1,3-butadienes to 4-vinylcyclohexene or a substituted derivative thereof.

4-Vinylcyclohexene (hereinafter referred to as vinylcyclohexene) and substituted vinylcyclohexenes are useful starting materials for the synthesis of styrene and substituted styrenes. Styrene is a well-known monomer for polystyrene plastics and composites.

Vinylcyclohexene can be prepared by an uncatalyzed thermal dimerization of butadiene. Disadvantageously, this process yields a mixture of products including vinylcyclohexene, 1,5-cyclooctadiene and polymeric butadienes, which must be separated to obtain the desired vinylcyclohexene product.

Catalyzed processes are also known for the dimerization of butadiene. For example, British Patent 1,554,942 and U.S. Pat. No. 4,125,483 disclose a process for the catalytic dimerization of butadiene to vinylcyclohexene in the presence of a cation-exchangeable aluminosilicate into which copper(I) ions and ions of an alkali metal having an atomic number of at least 19, preferably, cesium, have been introduced. The aluminosilicate includes natural and synthetic zeolites, such as faujasite, as well as clay minerals, such as montmorillonite, and other synthetic silica aluminas. It is taught that copper is introduced into the aluminosilicate via ion-exchange with a copper(I) or copper(II) salt.

U.S. Pat. No. 3,444,253 also discloses the dimerization of butadiene to vinylcyclohexene in the presence of copper(I) zeolites X or Y. The catalyst is taught to be prepared by ion-exchange of sodium zeolite X or Y with cuprous iodide in liquid ammonia or by the reduction of copper(II) zeolite X or Y with carbon monoxide, ammonia, acetylinic hydrocarbon or an olefinic hydrocarbon.

U.S. Pat. No. 4,665,247 relates to a process for the cyclodimerization of butadiene to vinylcyclohexene under Diels-Alder conditions in the presence of a copper-containing ZSM-12 zeolite catalyst. It is taught that the ZSM-12 zeolite is ion-exchanged or impregnated with copper(II) cation.

P. Renger F. Janowski, F. Wolf and E. Jahn report in Z. Chem, 19, (1979), 194–195, that butadiene is cyclodimerized to vinylcyclohexene in the presence of silica gel impregnated with copper(II) ions.

All of these processes suffer from the same manifold disadvantages. First, and most importantly, the lifetime of these catalysts is short, and the catalyst easily deactivates from coking and fouling. second, the preparations of the catalysts are difficult and expensive. For example, the catalysts prepared by ion-exchange with copper(II) salts must be reduced to the copper(I) oxidation state, which is the active form of the catalyst. Disadvantageously, the reduction process is inefficient. Alternatively, the catalysts may be prepared without reductants by ion-exchange with copper(I) salts; however, this route is disadvantageous because copper(I) salts oxidize easily and are not readily solubilized without expensive solubilizing ligands. Third, the regeneration of these catalysts typically requires burning off the coked material at high temperatures, typically at least about 400° C.; however, such a procedure oxidizes copper(I) to copper(II), and therefore a reduction procedure is again necessitated to bring the catalyst back into the active cuprous form. Finally, in certain instances the catalysts may possess low activity and even low selectivity.

It would be desirable to have a highly active catalyst for the dimerization of butadiene to vinylcyclohexene. It would be advantageous if such a catalyst could be easily prepared without expensive solubilizing ligands and without an additional and inefficient reduction step. It would be even more advantageous if such a catalyst did not rapidly coke and deactivate, but rather possessed a long lifetime. Finally, it would be most advantageous if such a catalyst could be regenerated easily and without a separate reduction procedure.

SUMMARY OF THE INVENTION

In one aspect this invention is a first process for the cyclodimerization of 1,3-butadiene or substituted 1,3-butadienes to 4-vinylcyclohexene or a substituted derivative thereof. The process comprises contacting 1,3-butadiene or a substituted 1,3-butadiene with a catalytic amount of copper(I) ions supported on a carrier. The contacting also occurs in the presence of a promoting amount of a hydroxylic solvent and under reaction conditions such that the activity of the catalyst, as measured by the rate of formation of vinylcyclohexene, is increased when compared to a control process conducted with a minimum level of hydroxylic solvent. The control process and minimum hydroxylic solvent level are described in detail hereinafter.

In another aspect this invention is a second process for the cyclodimerization of 1,3-butadiene or substituted 1,3-butadienes to 4-vinylcyclohexene or a substituted derivative thereof. The process comprises contacting 1,3-butadiene or a substituted 1,3-butadiene with a catalytic amount of a copper(I)-impregnated aluminosilicate zeolite under reaction conditions such that vinylcyclohexene or a substituted derivative thereof is formed in high selectivity. The zeolite is selected from the group consisting of faujasite zeolites, mordenite, zeolite L, zeolite omega ($\Omega$) and zeolite beta ($\beta$). In addition, the catalyst half-life is at least about 500 hours.

The processes of this invention produce vinylcyclohexenes in a steady high rate of formation, heretofore not possible with the catalysts of the prior art. Vinylcyclohexenes are valuable as precursors to styrenes. In addition, the preferred catalyst in the process of this invention possesses many advantageous features, described hereinbelow.

In a third aspect, this invention is a catalyst composition comprising copper(1) ions impregnated onto an aluminosilicate zeolite. The zeolite is selected from the group consisting of faujasites, mordenite, zeolite L, zeolite omega ($\Omega$), and zeolite beta ($\beta$). The zeolite is characterized by a silica to bulk alumina molar ratio in the range from about 5 to about 50, and a silica to tetrahedral framework alumina molar ratio of at least about 15. The "bulk" ratio includes alumina from both tetrahedral framework sites as well as excess or non-framework alumina located in the pores. Optionally, the catalyst composition contains a binder.

In a fourth aspect, this invention is a method of preparing the above-identified catalyst comprising (a) drying an aluminosilicate zeolite to remove water, the zeolite being selected from the group consisting of faujasites, mordenite, zeolite L, zeolite $\Omega$ and zeolite $\beta$ and being characterized by a silica to bulk alumina molar ratio in the range from about 5 to about 50 and a silica to framework alumina molar ratio of at least about 15, (b) impregnating the dried zeolite with a solution containing a soluble copper(II) salt, (c) calcining the copper(II)-impregnated zeolite under conditions such that the anion of the soluble salt is removed, (d) adding a hydroxylic solvent to the calcined zeolite in a concentration sufficient to increase the activity of the catalyst in the dimerization of 1,3-butadiene to 4-vinylcyclohexene, as compared with the activity of a similar catalyst which is essentially not hydroxylated, and (e) reducing the resulting hydroxylic solvent-treated copper(II)-impregnated zeolite under conditions such that a portion of the copper(II) ions are converted to copper(I).

The catalyst of this invention is useful in the aforementioned cyclodimerization of butadiene and substituted butadienes, and surprisingly maintains a long lifetime in that process before deactivating. A catalyst half-life on the order of at least about 500 hours is readily achieved. In addition, the aboveidentified catalyst is advantageously prepared without expensive solubilizing ligands. More advantageously, the preferred reduction step which is employed in preparing the catalyst of this invention is efficient and readily conducted insitu in the aforementioned dimerization process. Most advantageously, the catalyst of this invention is easily regenerated. All that is required is an oxygen burn-off at low temperatures, typically less than about 325° C., followed by rehydration, and the activity of the catalyst is restored essentially to its original level. Consequently, the combined beneficial properties of the catalyst of this invention make it desirable for commercial applications.

Figure 1:
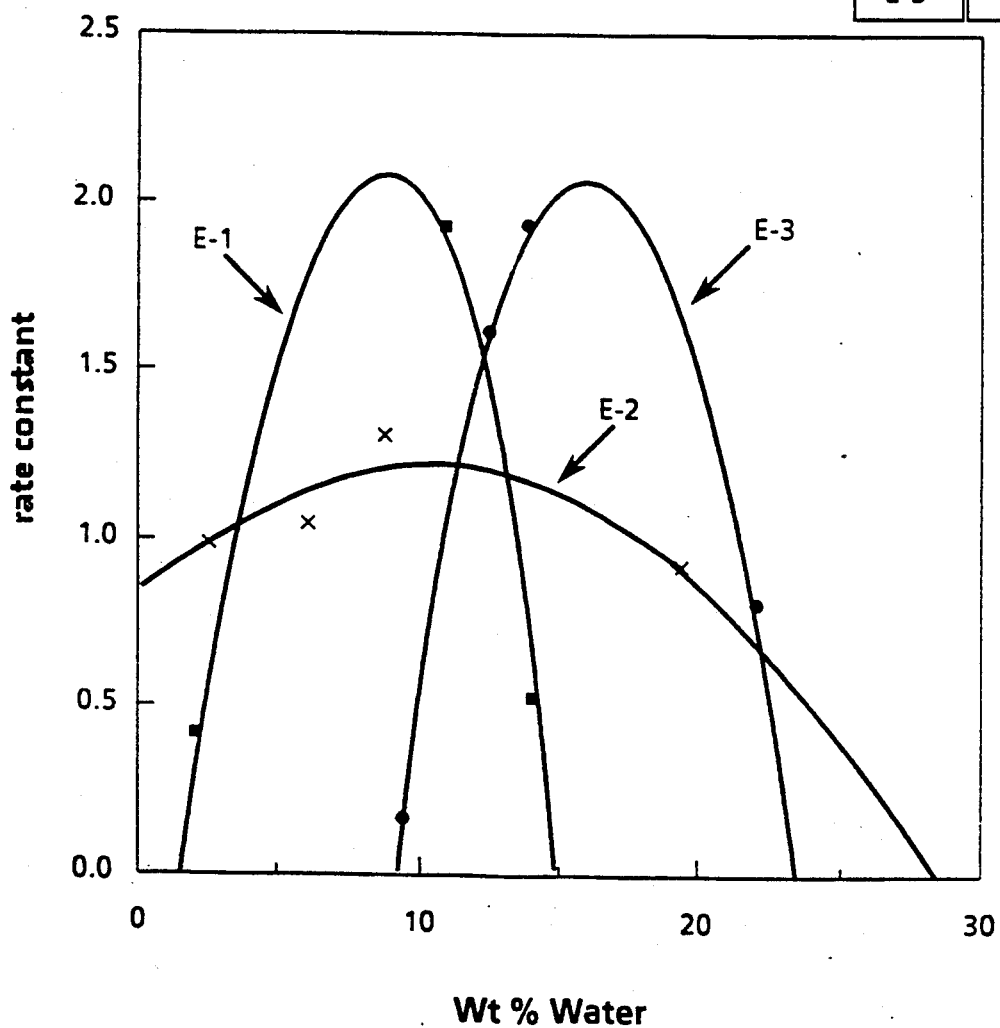
FIGS. 1, 2 and 3 depict graphs of the rate constant for the formation of vinylcyclohexene plotted versus the concentration of water in the catalyst, as described in detail in Examples E-1a-b, E-2a-d, E-3a-f, E-5a-i, and E-10a-f.

DETAILED DESCRIPTION OF THE INVENTION 1,3-Butadiene or a substituted 1,3-butadiene is required for the cyclodimerization processes of this invention. 1,3-Butadiene may be obtained from any hydrocarbon source. Crude C4 hydrocarbon feedstreams obtained from petroleum crackers are suitable. Preferably, the crude C4 hydrocarbon stream contains from about 10 volume percent to about 80 volume percent 1,3-butadiene. The balance of such streams comprises predominantly butane with lesser amounts of butenes, methylallene, methylacetylene, and other C4 compounds. More preferably, the concentration of butadiene in the feedstream ranges from about 30 volume percent to about 50 volume percent. Optionally, it may be desirable to purify the crude C4 hydrocarbon stream over a copper hydrogenation catalyst, such as a KLP-type catalyst, to remove acetylenic components which may cause a problem in the cyclodimerization process.

Substituted 1,3-butadienes are also suitable for the cyclodimerization processes of this invention. The substituent may be situated at any carbon along the butadiene chain, but preferably is substituted at the 2-carbon. The substituent is required to be inert, meaning that it does not inhibit the cyclodimerization process of this invention. Suitable substituents include alkyl moieties, preferably containing from 1 to about 10 carbon atoms, as well as halo moieties, such as chloro and bromo, and amino, nitro, and hydroxyl moieties. Non-limiting examples of substituted 1,3-butadienes include isoprene and chloroprene. Preferably, the substituted 1,3-butadiene is isoprene.

Optionally, a liquid diluent can be employed with the above-identified butadiene feedstream. The primary function of the diluent is to reduce the concentration of vinylcyclohexene in the product stream, because at high concentrations vinylcyclohexene can reduce catalytic activity. Such liquid diluents should be stable and inert with respect to the cyclodimerization processes of this invention. Suitable diluents include aromatic hydrocarbons, preferably, those having one aromatic ring and up to about 15 carbon atoms. Non-limiting examples include benzene, toluene, xylene, ethylbenzene, and propylbenzene; however, other solvents such as naphthalene, nitrobenzene, ethylene dichloride, n-butane and butenes are also suitable. Preferably, the diluent is ethylbenzene or propylbenzene. More preferably, the diluent is ethylbenzene. If a diluent is used, then the concentration of butadiene in the feedstream containing the diluent ranges, preferably, from about 10 volume percent to about 80 volume percent, as noted hereinbefore. Below about 10 volume percent, the conversion of butadiene may be too low and the process may be economically unfeasible. Above about 80 volume percent, the process may be difficult to control and the high concentration of vinylcyclohexene product may reduce catalytic activity.

A hydroxylic solvent is required for the first cyclodimerization process of this invention. The hydroxylic solvent is any liquid containing hydroxyl moieties, such as water and alcohols. Preferred alcohols are lower molecular weight mono-alcohols containing up to about five carbon atoms, such as methanol, ethanol, n-propanol, i-propanol, t-butanol, n-pentanol, and the like. More preferably, the hydroxylic solvent is water or an alcohol containing up to about three carbon atoms. Most preferably, the hydroxylic solvent is water or methanol.

The hydroxylic solvent may be added either to the feedstream or to the catalyst. Preferably, however, the hydroxylic solvent is initially added to the catalyst, and the feedstream is kept just hydroxylated enough to maintain the desired hydroxyl level on the catalyst under the operating conditions of the process. Preferably, the concentration of the hydroxylic solvent in the feedstream is less than about 250 ppm, more preferably, less than about 100 ppm, most preferably less than about 50 ppm. A detailed description of how hydroxylic solvent is introduced into the catalyst is given hereinafter.

The catalyst employed in the process of this invention comprises copper(I) ions supported on a carrier. The carrier may be a crystalline aluminosilicate zeolite, a non-zeolitic amorphous alumina-silica mixture, silica, silica gel, alumina, or a clay mineral, such as montmorillonite. Preferably, the carrier is a crystalline aluminosilicate zeolite, any of the natural or synthetic varieties of which is suitable. More preferably, the carrier is selected from the group consisting of faujasite zeolites, mordenite, zeolite omega ($\Omega$), zeolite L and zeolite beta ($\beta$). Even more preferably, the zeolite is selected from the group consisting of faujasite zeolites and zeolite L; and most preferably, faujasite zeolites X and Y. Copper ions may be introduced onto the support by techniques known to those skilled in the art, for example, ion-exchange or impregnation. These techniques are illustrated in detail hereinafter for the preferred case of a zeolite carrier.

The starting zeolite may be selected in an acid form or in a salt form, wherein the cation is typically an ion from the Group IA or IIA metals, such as sodium or magnesium ions. While any silica to bulk alumina molar ratio ($SiO_2/Al_2O_3$) is acceptable, the preferred starting zeolite has a bulk $SiO_2/Al_2O_3$ molar ratio ranging from about 5 to about 50. The aforementioned "bulk" ratio includes alumina from both tetrahedral framework sites as well as excess or non-framework alumina located in the pores. More preferably, the bulk $SiO_2/Al_2O_3$ molar ratio ranges from about 10 to about 45, most preferably, from about 12 to about 30. Below the preferred bulk $SiO_2/Al_2O_3$ molar ratio of about 5 the catalyst may have acceptable activity, but may exhibit a reduced lifetime. Above the preferred bulk $SiO_2/Al_2O_3$ molar ratio of about 50 the catalyst may have an acceptable lifetime, but may exhibit reduced activity. If only the tetrahedral framework alumina is considered, the preferred framework $SiO_2/Al_2O_3$ molar ratio is at least about 15, more preferably, at least about 22.

The starting zeolite carriers of this invention are available commercially or can be synthesized according to procedures well documented in the art. See, for example, *Zeolite Molecular Sieves* by Donald W. Breck, John Wiley & Sons, 1974, and references therein. Zeolite carriers, such as the faujasites, mordenite, zeolite L and zeolite $\Omega$, normally contain a significant quantity of water. For example, the faujasites, taken as the sodium salt, typically can be represented by an oxide formula $Na_2O.Al_2O_3.4.5SiO_2.7H_2O$ which corresponds to a saturation water content of about 23 weight percent. Mordenite, taken as the sodium salt, typically can be represented by an oxide formula $Na_2O.Al_2O_3.10SiO_2.6H_2O$ corresponding to a saturation water content of 12 weight percent. Zeolite L, taken as the sodium salt, can be represented by an oxide formula $Na_2O.Al_2O_3.6SiO_2.5H_2O$ which corresponds to a saturation water content of about 15 weight percent. Zeolite $\Omega$, also taken as the sodium salt, can be represented by an oxide formula $Na_2O.Al_2O_3.7SiO_2.5H_2O$, which corresponds to a saturation water content of about 13 weight percent. Unexpectedly, it has now been discovered that the concentration of water affects the activity of the catalyst in the process of this invention, and that the aforementioned saturation level of water normally found in zeolites is detrimental to the activity of the catalyst.

Generally, therefore, the starting zeolite is dried prior to preparing the catalyst composition. This drying procedure is optional, but functions to remove most of the water from the zeolite. Drying is usually effected at a temperature in the range from about 50° C. to about 450° C., and preferably in a range from about 100° C. to about 300° C., for a time ranging from about 1 hr to about 24 hr. Drying the zeolites to very low levels of water content, however, does not generally produce a sufficiently active catalyst for the process of this invention. It has now been discovered that the water content of the zeolite carrier must be maintained within a carefully controlled range in order to obtain optimum catalyst activity.

The carrier may be used as is or may be composited with a binder into extrudate or pellets for added strength and durability. Binders such as silica, and alumina are suitable. Preferably, the binder is alumina. The size of the extrudate or pellets suitably ranges from about ⅛ inch to about ½ inch at largest dimension.

As noted hereinbefore, copper(1) ions are an essential component of the catalyst. Ion-exchange or impregnation techniques, defined hereinafter, may be employed to introduce copper into the zeolite. Typically, however, a water-soluble copper(II) salt is employed because copper(I) salts are not sufficiently soluble or stable, especially in water. It will be immediately obvious that if a copper(II) salt is introduced into the zeolite, then a reduction step is required to obtain copper(I), the more active form of copper.

The term "ion-exchange" is taken to mean a technique whereby metal ions, specifically copper ions in this case, actually replace a portion or essentially all of the hydrogen ions or cations of the zeolite. Ion-exchange is easily effected by stirring or slurrying the zeolite with an excess of a solution containing a soluble copper(II) salt. Non-limiting examples of suitable solutions include aqueous solutions of cupric nitrate, sulfate or acetate. The concentration of such solutions will vary depending upon the desired degree of ion-exchange, but typically range from about 0.01 M to about 10 M. Heat may be applied to enhance the replacement reaction. Typical temperatures range from about ambient to the boiling point of the solvent, preferably from about 50° C. to about 100° C. The slurrying time will depend upon the size of the batch, and therefore can vary widely. Generally, at least about 2 hours is required. Ion-exchange techniques are described by D. W. Breck in Molecular Sieves: Structure, Chemistry and Use, Wiley-Interscience, 1974, Chapter 7, which is incorporated herein by reference. Alternatively, the catalyst may be prepared by direct ion-exchange with a copper(1) salt dissolved in liquid ammonia.

Optionally, when the catalyst is prepared by ion-exchange techniques the zeolite may be ion-exchanged first with a Group IIA alkaline earth metal ion and thereafter ion-exchanged with a copper(II) salt. It is believed that the alkaline earth ions prohibit copper ions from migrating into deep, inaccessible sites in the zeolite where they may be less catalytically active. Such a theory, however, should not be binding. The preferred alkaline earth ions include magnesium, calcium, strontium, and barium ions, more preferably, calcium ions. The ion-exchange procedure is carried out with a soluble salt of the alkaline earth metal, for example, the nitrate, sulfate or acetate, in accordance with the exchange procedure described hereinbefore. The concentration of calcium ions in the zeolite ranges from about 0.05 to about 10 weight percent.

For the purposes of this invention, "impregnation" refers to a technique whereby a metal salt, in this instance a soluble copper(II) salt, is deposited on the surface and throughout the pore structure of the zeolite, but predominantly on the surface. Hence, after impregnation the zeolite contains the anion of the salt in addition to copper(II). Impregnation can be effected by dipping the zeolite into an excess of a solution of a copper salt, such as the nitrate, acetate or sulfate. Preferably, more precise control is achieved by a technique called "dry impregnation" or "impregnation to incipient wetness." In this method the zeolite is sprayed with a quantity of the copper(II) solution corresponding to the total known pore volume, or slightly less. The dry impregnation technique is described by Charles N. Satterfield in *Heterogeneous Catalysis in Practice* McGraw-Hill Book Company, 1980, p. 82-83, and is incorporated herein by reference. Alternatively, it is possible to impregnate the support with a copper(I) salt; however, this method of catalyst preparation is not preferred because, as noted hereinbefore, copper(I) salts are not readily solubilized.

Impregnation with a copper (II) salt is the preferred method of preparing the catalyst composition of this invention, because the impregnated composition has greatly improved properties. Specifically, the impregnated catalyst is easily prepared without the use of expensive ligands. In addition, as shown hereinafter, the impregnated catalyst is easily reduced in situ in the dimerization reaction thereby eliminating a separate reduction step. Thirdly, the impregnated catalyst is easily regenerated by a simple burn-off at low temperatures followed by rehydration. Finally, the impregnated catalyst possesses a long lifetime.

The concentration of copper(II) ions introduced into the carrier may be any concentration which yields a catalyst of high activity in the process of this invention, as defined hereinafter. Generally, the concentration ranges from about 0.1 to about 10 weight percent, preferably, from about 2 to about 9 percent, more preferably, from about 3 to about 8 percent.

After the starting zeolite is ion-exchanged with copper(II) ions or impregnated with a copper(II) salt, the zeolite is usually dried at a temperature in the range from about 50° C. to about 120° C. to remove excess and adsorbed solvent.

At this stage, the preparation varies depending upon whether the carrier has been ion-exchanged or impregnated. An ion-exchanged carrier is reduced to convert a portion of the copper(II) ions to copper(I) ions. The reduction may be carried out with any reducing agent that is capable of this conversion. Nonlimiting examples of reducing agents include hydrogen, carbon monoxide, ammonia, hydrazine, and ascorbic acid. Preferably, the reducing agent is gaseous ammonia or hydrazine and a base, such as sodium hydroxide. More preferably, the reducing agent is ammonia. The reduction is conducted at a temperature in the range from about 200° C. to about 400° C. and a pressure from about atmospheric to about 5 psig. Typically, at least about 10 percent of the copper(II) ions available to the reductant are converted to copper(I), preferably, at least about 50 percent of the copper(II) ions available to the reductant are converted to copper(I).

In contrast, an impregnated zeolite is not reduced at this stage, but rather is calcined to destroy or oxidize the anion of the copper salt. The calcination is conducted at a temperature in the range from about 200° C. to about 325° C., preferably from about 250° C. to about 300° C., for a time ranging from about 1 hr to about 24 hr. Advantageously, the impregnated zeolite needs no separate reduction step to convert copper(II) to copper(I), because the impregnated cupric ions are efficiently reduced by butadiene insitu in the cyclodimerization reaction. In the preferred embodiment the catalyst is prepared by impregnation and reduced in situ.

A promoting amount of hydroxylic solvent, such as water, is required for the first dimerization process of this invention. The hydroxylic solvent functions to increase the activity of the catalyst, as measured by an increase in the rate of formation of vinylcyclohexene. The hydroxylic solvent may be added in the liquid or vapor phase to the "dried" form of the ion-exchanged or impregnated carrier, the "dried" form of the zeolites being obtained in the preparations described hereinabove. Specifically, during the aforementioned calcination of the copper(II)-impregnated zeolite to remove the anion of the copper salt, water is also removed yielding an essentially dry zeolite containing no greater than about 2 weight percent water. Likewise, during the aforementioned reduction of the ion-exchanged zeolite with ammonia or hydrazine, water is also removed yielding a zeolite containing similarly low levels of water. Some carriers in the "dried" form may contain essentially no water, and even zeolites if handled with special precaution can be dried to water levels lower than 2 weight percent. To hydroxylate the impregnated or reduced ion-exchanged carrier, the dried material is exposed to a humidified vapor, such as ambient air or a moist stream of nitrogen, for a time sufficient to adsorb the desired concentration of water. Alternatively, a predetermined amount of alcohol may be added to the dried impregnated or ion-exchanged carrier.

The concentration of hydroxylic solvent introduced into the copper(II)-treated carrier may be any concentration which achieves an increase in the rate of formation of vinylcyclohexene, as compared with a control process described hereinafter. The concentrations which achieve this effect vary depending upon the type of carrier, the copper loading, the manner in which copper ions are introduced into the carrier, its $SiO_2/Al_2O_3$ molar ratio (where applicable), and whether alkaline earth cations are present. Roughly, the promoting hydroxyl concentration is in the range from about one-third to about one-half of the saturation water concentration of the specific zeolite employed, as determined by thermal gravimetric analysis (TGA). In the case of a copper-exchanged faujasite zeolite the promoting amount of water varies from about 2.5 weight percent to about 22 weight percent of the catalyst composition depending upon the method of copper introduction and reduction. For example, the more preferred water concentration for a copper(II)-exchanged zeolite reduced with liquid ammonia ranges from about 4 to about 14 weight percent; whereas, the more preferred concentration for a copper(II)-exchanged zeolite reduced with hydrazine ranges from about 10 to about 21 weight percent. Below the lower concentrations and above the upper concentrations, the activity of the catalyst, as measured by the rate of formation of vinylcyclohexene, may decrease significantly. In the preferred form of the catalyst comprising a copper(I)-impregnated faujasite zeolite the water concentration preferably ranges from about 3 to about 14 weight percent, more preferably, from about 4 to about 12 weight percent, and most preferably, from about 7 to about 9 weight percent. Variations in the optimum range of water concentration are within the scope of this invention and may have to be determined by one skilled in the art.

Additionally, it is preferred that the copper(1)-impregnated catalyst of this invention is essentially free of chloride and certain metals or metal ions, specifically, zinc and chromium. By "essentially free" is meant that the concentration of these components in the catalyst is less than about 1 weight percent, more preferably, less than about 0.5 weight percent, most preferably, less than about 0.1 weight percent.

Advantageously, the preferred copper(1)-impregnated catalyst of this invention exhibits a long lifetime before loss of activity. Typically, the catalyst half-life ($\tau_{\frac{1}{2}}$) is at least about 500 hours. Preferably, the catalyst half-life is at least about 800 hours, more preferably, at least about 1000 hours, and most preferably, at least about 1500 hours.

When any catalyst of this invention has lost sufficient activity so as to render it uneconomical, the deactivated catalyst is easily regenerated by calcination in the presence of air at a temperature in the range from about 200° C. to about 500° C. for a time sufficient to render the catalyst active again, usually overnight. Preferably, the calcination temperature ranges from about 250° C. to about 350° C. for impregnated catalysts and from about 350° C. to about 450° C. for ion-exchanged catalysts. The heating functions to burn off polymeric butadienes and coke, but also oxidizes copper(I) to copper(II). The oxidized composition must therefore be reduced to the catalytically active copper(I) form. In addition, the oxidized composition must be rehydroxylated to readjust the water concentration to within the desired range. In the case of the ion-exchanged catalyst, the reduction is carried out as described hereinbefore, for example, with ammonia or hydrazine, and then the rehydroxylation is effected. In the case of the preferred impregnated catalyst, the rehydroxylation is carried out first, and the reduction is efficiently achieved in situ by butadiene in the dimerization process of this invention.

Butadiene or substituted butadienes can be contacted with the catalyst of this invention in a reactor of any configuration, including batch-type reactors and continuous flow reactors, such as continuous plugged flow reactors, continuous stirred tank reactors (CSTR), fluidized bed reactors, riser reactors, and the like. Preferably, the reactor is a continuous plugged flow reactor. The feedstream containing the butadiene may be maintained in the gaseous or liquid states, preferably, the liquid state.

Any operable temperature is suitable for the dimerization processes of this invention provided that the process yields a vinylcyclohexene product in high selectivity. Typically, the process temperature ranges from about 70° C. to about 170° C. Preferably, the temperature ranges from about 80° C. to about 150° C., more preferably, from about 100° C. to about 130° C. Below the preferred lower temperature, the conversion may be too low, and the process may become uneconomical. Above the preferred upper temperature the rate of reaction may be too high and the reaction may be difficult to control. Such high temperatures may also lead to hot spots and coking of the catalyst, excessive volatilization of the feedstream, and formation of polymeric by-products.

Likewise, any operable pressure is suitable for the dimerization processes of this invention provided that the process yields a vinylcyclohexene product in high selectivity. Preferably, the pressure is high enough to maintain at least about 95 volume percent of the butadiene reactant in the liquid phase at the operating process temperature. Suitable pressures are those greater than about 100 psig. Preferably, the pressure ranges from about 100 psig to about 1000 psig, more preferably, from about 200 psig to about 600 psig, most preferably, from about 300 psig to about 500 psig. Below the lower preferred pressure, excessive volatilization may occur. Above the upper preferred pressure, special high pressure equipment may be required and the process may be uneconomical.

The butadiene feedstream is contacted with the catalyst for a time sufficient to cyclodimerize the butadiene to vinylcyclohexene in high selectivity. Typically, the residence time is determined by the weight hourly space velocity, expressed in units of grams butadiene feed per gram catalyst per hour, or simply $hr^{-1}$. Typically, the weight hourly space velocity ranges from about 0.01 $hr^{-1}$ to about 100 $hr^{-1}$, preferably from about 0.1 $hr^{-1}$ to about 10 $hr^{-1}$, more preferably, from about 0.5 $hr^{-1}$ to about 5.0 $hr^{-1}$.

When 1,3-butadiene or substituted butadiene is contacted with the catalyst of this invention in the manner described hereinbefore, the butadiene is cyclodimerized to 4-vinylcyclohexene or a substituted derivative thereof. Typically, this process occurs with high selectivity, therefore, few if any by-products are produced Polymerization of butadiene, for example, is usually small. It is typical to find less than about 1 mole percent of the converted butadiene in the form of polymeric butadienes. The chief by-products are tetrahydroethylnaphthalenes, which are also usually found in less than about 1 mole percent concentration.

For the purposes of this invention, the term "conversion" refers to the mole percent of butadiene or substituted butadiene which reacts to form products. Generally, in a continuous flow reactor the one pass conversion is at least about 30 mole percent. Preferably, the one pass conversion is at least about 50 mole percent, more preferably at least about 60 mole percent. Unconverted butadiene can be separated from the product stream via distillation and recycled back to the dimerization reactor.

For the purposes of this invention, the term "selectivity" refers to the mole percent of converted butadiene or substituted butadiene which forms vinylcyclohexene or a substituted derivative thereof. As noted hereinbefore, by-products are few. Consequently, the selectivity for vinylcyclohexenes is high. Typically, the selectivity for vinylcyclohexenes is at least about 95 mole percent, preferably, at least about 97 mole percent, more preferably, at least about 99 mole percent, and most preferably at least about 99.5 mole percent.

A convenient measure of the activity of the catalyst of this invention is given by the rate constant for the formation of vinylcyclohexene or substituted vinylcyclohexene. Generally, the dimerization process of this invention follows second order rate kinetics, as illustrated by a linear plot of inverse butadiene concentration (1/BD) versus time. The slope of the plot yields the bimolecular rate constant, k, given in units of (mole-hr)$^{-1}$ for a standard test composition. A discussion of second order rate phenomena can be found in Kinetics and Mechanism by A. A. Frost and R. G. Pearson, John Wiley and Sons, Inc., 1961, pp. 8-20. In special cases, such as at high initial butadiene concentrations of at least about 40 mole percent in the feedstream, deviation from second order kinetics is observed. In this case and for the purposes of this invention, the second order rate constant is referred to as the "apparent" bimolecular rate constant.

The rate constant for the formation of vinylcyclohexene in the processes of this invention varies widely depending upon the process conditions and the form of the catalyst, specifically, the type of carrier and the method of catalyst preparation. A typical bimolecular rate constant (k) for the dimerization process of this invention when conducted at 100° C. is at least about 0.2 (moles-hr)-1 for the standard feed composition described hereinbelow in Example 1a-b, and may be as high as about 2.5 (moles-hr)$^{-1}$. Preferred rate constants will depend on economic considerations, and even rate constants as low as 0.2 (moles-hr)$^{-1}$ are commercially feasible provided that the lifetime of the catalyst is long, as is the case in the preferred impregnated catalyst of this invention.

In accordance with the first process of this invention, a promoting amount of hydroxylic solvent causes the rate constant for the formation of vinylcyclohexene to increase, as compared with the rate constant of a control process. The control process is identical to the process of this invention with one exception. Rather than employing a promoting amount of hydroxylic solvent, the control process operates at a minimum of hydroxylic solvent. By "minimum of hydroxylic solvent" is meant that the concentration of hydroxylating solvent in the catalyst of the control is no greater than about 2 weight percent. In all other aspects the control process is identical to the process of this invention. For example, the control catalyst is prepared with the same components and same procedures as the catalyst of the invention with the exception that the catalyst is not treated with hydroxylic solvent. Moreover, the process conditions of the control reaction, including the butadiene feedstock, temperature, pressure, flow rate, reactor design, and the like, are identical to the conditions of the process invention.

When the rate constant for the formation of vinylcyclohexene of the first process of this invention is compared with the rate constant of the abovedescribed control process, it is seen that the rate constant of the process of this invention is higher. The increase depends upon the specific process conditions and the specific catalyst employed and therefore varies widely. Increases in the rate constant as low as about 25 percent are possible, as are increases as high as about 500 percent. Preferably, the increase in rate constant is at least about 50 percent, more preferably at least about 100 percent, and most preferably, at least about 250 percent.

ILLUSTRATIVE EMBODIMENTS

The following illustrative embodiments are representative of the process and catalyst of this invention, but are not intended to be limiting thereof. Unless otherwise noted, all percentages are given as weight percent.

Preparation of Cu(+1) Ion-exchanged Zeolite Catalysts

A copper(+1) ion-exchanged zeolite catalyst is prepared according to the following general procedure: A developmental crystalline aluminosilicate zeolite Y with 15 weight percent silicate binder (UOP LZY-54; 140 g) is dried at 350° C. for 60 hr in a muffle furnace. The heated catalyst is loaded into a three-neck, one-liter glass reactor equipped with a dry ice condenser and solids addition funnel. The reactor system is flushed with pre-purified nitrogen and evacuated three times. Liquid ammonia is condensed into the reactor until the catalyst pellets are just covered; thereafter copper(I) iodide (37 g: 0.29 moles) is added to the reactor. Nitrogen is sparged into the reactor to effect agitation, and the ammonia is allowed to reflux for three hours. Afterwards, the liquid ammonia is removed from the bottom of the reactor and the pellets are washed once with ammonia. A second charge of copper iodide (37 g; 0.29 moles) and liquid ammonia is added and reflux is continued for another three hours. The reactor is drained and the pellets are washed twice with about 60 ml of liquid ammonia. The pellets are loaded into a tubular reactor and the residual ammonia is removed at 350° C. with flowing nitrogen yielding a dried copper(+1) ion-exchanged zeolite catalyst with a copper loading of 6.6 weight percent. The water content of the dried catalyst is 2.13 percent, as determined by thermogravimetric analysis (TGA). The dried catalyst is control sample C-1. Two samples of the dried catalyst (4.75 g) are allowed to adsorb water vapor from a wet nitrogen atmosphere for a time sufficient to obtain hydrated catalysts E-1-a and E-1-b having the water concentrations shown in Table I.

TABLE I

| Sample | Wt. % H$_2$O | k (mole-hr)$^{-1}$ |
|---|---|---|
| C-1 | 2.130 | 0.420 |
| E-1-a | 10.900 | 1.930 |
| E-1-b | 14.000 | 0.531 |

EXAMPLE E-1-a-b

Dimerization of Butadiene to Vinylcyclohexane

The control and hydrated catalysts (C-1, E-1-a and E-1-b) prepared hereinabove are tested in the dimerization of butadiene (BD) according to the following general procedure: The catalyst (4.75 g) is placed in an annular basket in a 300 cc Parr reactor equipped with overhead stirring, a sampling dip tube, and a thermocouple for measuring temperature. The reactor is further loaded with 100 cc of ethylbenzene. The reactor is sealed, and thereafter purged three times with 400 psig of nitrogen, and then vented to atmospheric pressure Butadiene (28.9 g, 0.535 moles) is added as a liquid. The reactor is pressurized to 440 psig with nitrogen and the temperature is raised to 100° C. The contents are sampled at various times by emptying a sample loop into a pre-weighed, septum-sealed sample vial containing hexane, as a diluent, and an internal standard, and then analyzed on an FID capillary gas chromatograph. Vinylcyclohexene is formed in a selectivity of about 99 mole percent. The second order rate constant for the formation of vinylcyclohexene is determined by a least squares fit to data plotting inverse butadiene concentration (1/BD) versus time. The rate constants are set forth in Table I and plotted versus water concentration in FIG. 1.

It is observed that a copper(I) ion-exchanged faujasite zeolite catalyzes the cyclodimerization of butadiene to vinylcyclohexene in high selectivity. Further, the rate constant of the control experiment C-1 is seen in FIG. 1 to be significantly less than the rate constant of the hydrated catalyst E-1-a and slightly less than the rate constant of the hydrated catalyst E-1-b. The rate constant is observed to peak at a water concentration of about 8 percent. FIG. 1 also shows that it is impractical to operate the cyclodimerization process with the catalyst of E-1 at water concentrations less than about 2 percent or greater than about 15 percent.

Preparation of Calcium (II) and Copper(II) Ion-exchanged Zeolite, Pre-reduced with Ammonia A pelletized zeolite Y (100 g; UOP LZY-54) bound with 15 percent silicate is ion-exchanged with 1.5 L of a 0.1 M calcium acetate solution for 4 hr at 25° C. Thereafter, the ion-exchanged zeolite is washed with 3 L of deionized water, dried at 110° C. overnight and calcined at 500° C. for 18 hr. The pellets are ionexchanged a second time with 2 L of the 0.1 M cupric acetate solution for 18 hr. The ion exchange procedure is repeated twice for 2 hr each to give a concentration of 3.61 percent copper(II). The ion-exchanged zeolite is washed with 4 L of deionized water and dried a second time at 100° C. overnight. The dried zeolite is reduced with gaseous ammonia (5 vol. percent in nitrogen) for 1 hr at 250° C., and then stripped at that temperature for 30 min under a nitrogen flow. Samples of the reduced and dried pellets are hydrated to a predetermined concentration of water in a moist nitrogen atmosphere as set forth in Table II.

TABLE II

| Sample E-2 | Wt. % $H_2O$ | k $(mole-hr)^{-1}$ |
|---|---|---|
| a | 2.570 | 0.990 |
| b | 6.000 | 1.051 |
| c | 8.690 | 1.310 |
| d | 19.400 | 0.927 |

EXAMPLES E-2A-D

Cyclodimerization of Butadiene to Vinylcyclohexene

The ion-exchanged and hydrated pellets E-2a-d (4.0 g), prepared hereinabove, are employed as catalysts in the cyclodimerization of butadiene according to the procedure described in E-1 with the results shown in Table II and FIG. 1. Vinylcyclohexene is produced in a selectivity of at least 99 mole percent.

It is observed that a calcium and copper(II) ion-exchanged faujasite zeolite pre-reduced with ammonia catalyzes the cyclodimerization of butadiene to vinylcyclohexene in high selectivity. It is seen in FIG. 1 that the plot for Example E-2 is broad and flat, whereas the plot for Example E-1 is narrow and sharp. This comparison suggests that water affects the rate constant of catalyst E-1, which contains no calcium, more significantly than the rate constant of catalysts E-2a-d, which contain calcium. However, the increase in rate constant for catalysts E-2a-d is observed over a wider range of water concentration than the increase observed for E-1. The plot also shows that it is impractical to practice the cyclodimerization process with catalysts E-2a-d at water concentrations greater than about 25 percent.

Preparation of Copper(II)-Ion-Exchanged Zeolite, Prereduced with Hydrazine

Sodium zeolite Y-52 (77 g, Union Carbide), undried, is slurried in 250 cc of a 0.5 M solution of cupric nitrate for 1 hour at room temperature. The mixture is filtered and washed once with 20 cc of deionized water. This procedure is repeated five times with the last set of washings being repeated until the filtrate is colorless. The resulting solid is dried for 2 hours in a nitrogen bled vacuum oven (20 mm Hg) at 2° C. The dried, ion-exchanged zeolite containing 8.78 weight percent copper (5 g, 6.9 mmoles $Cu^{+2}$) is added to 22 cc of a 0.35 M solution of sodium hydroxide and the slurry is degassed with nitrogen for 30 minutes. An 85 weight percent solution of hydrazine hydrate (11.5 μl) is added to the slurry at 25° C., and an immediate color change to green is observed. After 30 minutes another 11.5 μl of the same hydrazine solution is added, and after another 30 minutes a third addition of hydrazine solution (11.5 μl) is added bringing the color to a yellow gold. The slurry is stirred for 2 hours and filtered, and the resulting solid is washed with water and dried in the nitrogen-purged vacuum oven for 2 hours at 110° C. to yield a copper (11)-ion-exchanged zeolite pre-reduced with hydrazine. Samples of the aboveidentified zeolite are exposed to a moist atmosphere to obtain a predetermined moisture content as shown in Table III.

TABLE III

| Example | Wt. % $H_2O$ | k $(mole-hr)^{-1}$ |
|---|---|---|
| E-3-a | 9.400 | 0.170 |
| E-3-b | 12.500 | 1.590 |
| E-3-c | 12.500 | 1.618 |
| E-3-d | 12.500 | 1.613 |
| E-3-e | 13.900 | 1.935 |
| E-3-f | 22.04 | 0.810 |

EXAMPLE E-3a-f

Cyclodimerization of Butadiene to Vinylcyclohexene

The reduced compositions E-3a-f (4.0 g each) are employed as catalysts in the cyclodimerization of butadiene according to the procedure of Example E-1, with the exception that the process temperature is 115° C. Results are set forth in Table III and are plotted in FIG. 1. It is observed that the copper ion-exchanged faujasite zeolite pre-reduced with hydrazine catalyzes the dimerization of butadiene to vinylcyclohexene in high selectivity. When Example E-3 is compared with Example E-1, it is seen that the plots for each are both intense and sharp, but shifted along the x-axis (Wt. % $H_2O$) from each other. This result illustrates how the optimum water concentration varies with the method of preparing the catalyst. In addition, the plot shows that catalysts E-3a-f, which do not contain calcium, are significantly more dependent on water concentration than catalysts E-2a-d, which contain calcium. The plot also shows that it is impractical to run the dimerization process with catalyst E-3 at water concentrations less than about 9 percent and greater than about 24 percent.

EXAMPLE 4

A commercial zeolite powder (Union Carbide Y-52) is ion-exchanged three times with 0.5 M cupric nitrate solution. The ion-exchanged material is isostatically pressed into pellets at 30,000 psig with no addition of binder. The pellets are reduced with gaseous ammonia at 250° C., then stripped of adsorbed ammonia and dried under a helium flow at 250° C. for 30 minutes. The reduced pellets are thereafter hydrated to a concentration of 13.02 percent water in a moist nitrogen atmosphere. The catalyst is evaluated in the cyclodimerization of butadiene according to the procedure of Example E-1 and is found to have a second order rate constant of 0.39 $(mole-hr)^{-1}$.

EXAMPLE 5

(a) Preparation of Cu(11)-Impregnated Zeolite

Pellets (⅛" dia.) of a crystalline aluminosilicate zeolite (Union Carbide LZY-52) are made in ⅛" rubber tubing by isostatic compression at 30,000 psig of the as received solids without addition of a binder. This zeolite is in the sodium form, and has a $SiO_2/Al_2O_3$ molar ratio of 5/1. The pellets (5 g) are impregnated with 4.2 cc of a 1 M aqueous copper(II) nitrate solution. The impregnation is carried out on a watch glass where liquid and pellets are quickly mixed, and the moist pellets are place in a drying oven at 110° C. The pellets are gently stirred at the start of the drying period until visibly dry, and then they are dried further in the oven for several hours. The dried, impregnated zeolite contains 5.5 wt percent copper. Thereafter, the zeolite is calcined under air at a temperature of 275° C. overnight to remove or destroy the nitrate anion and to dry the zeolite further. The dried zeolite contains less than 2.0 percent water and is employed as a control (C-5) in the dimerization of butadiene, as noted hereinafter. Samples of the dried catalyst are hydrated by exposure to ambient air, as noted hereinafter, until a predetermined water concentration is obtained, as determined by TGA and as set forth in Table IV.

TABLE IV

| Sample | Wt. % $H_2O$ | $k$ (mole-hr)$^{-1}$ |
|---|---|---|
| C-5 | 2.000 | 0.070 |
| E-5-a | 3.400 | 0.110 |
| E-5-b | 4.000 | 0.114 |
| E-5-c | 4.800 | 0.170 |
| E-5-d | 5.100 | 0.136 |
| E-5-e | 5.300 | 0.170 |
| E-5-f | 6.900 | 0.162 |
| E-5-g | 8.900 | 0.186 |
| E-5-h | 12.100 | 0.127 |
| E-5-i | 9.800 | 0.169 | b) Cyclodimerization of Butadiene to Vinylcyclohexene

The control C-5 and hydrated zeolites E-5a-i, prepared hereinabove, are employed in the cyclodimerization of butadiene, as described in Example E-1. The zeolite is not pre-reduced, but rather is reduced to the active catalytic form in situ in the cyclodimerization process. After 4 hr into the cyclodimerization run and although the catalyst has not lost significant activity, the run is stopped and the catalyst is calcined at 275° C. under flowing air (22 cc/min) overnight. Thereafter the catalyst is exposed to ambient air until a predetermined water concentration is obtained. The hydrated catalyst is employed in the same dimerization reaction for another 4 hr, after which the run is stopped and the catalyst is re-calcined and re-hydrated to a new water concentration. Selection of the water concentration is random, and not in the order shown in Table IV. In such a manner a single batch of catalyst is run in the cyclodimerization, recovered, re-hydrated, and rerun in the dimerization to generate the data of Table IV, which data are plotted in FIG. 2. Vinylcyclohexene is produced in a selectivity of at least 99 mole percent.

Figure 2:
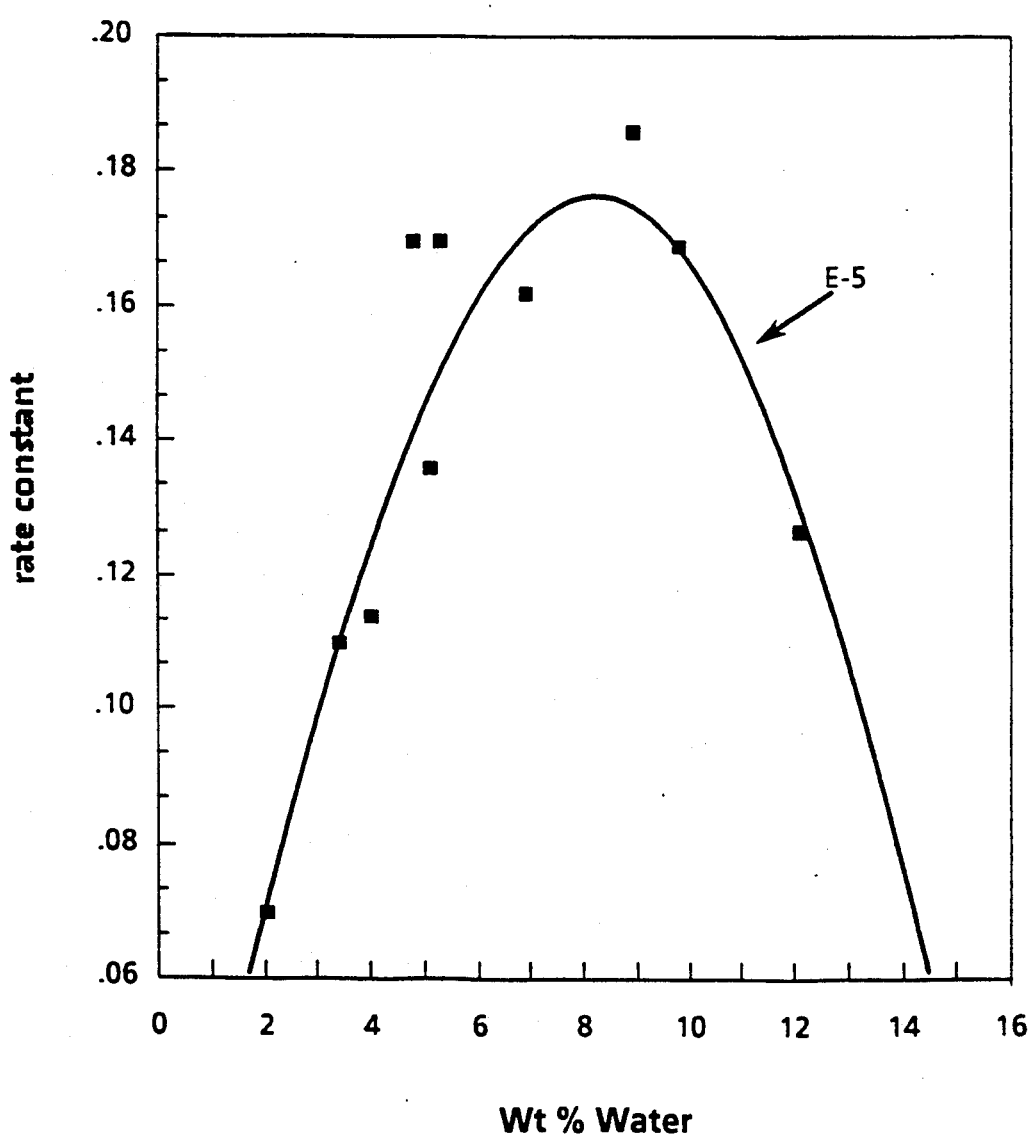

It is observed that the hydrated catalysts (E-5a-i) achieve a significantly higher rate constant for the formation of vinylcyclohexene than the dried control catalyst (C-5). Moreover, the rate constant is seen to peak at a water concentration of about 8 percent. FIG. 2 also shows that it is impractical to run the dimerization process with catalyst E-5 at a water concentration less than about 2 percent and greater than about 14 percent.

EXAMPLE 6

A catalyst is prepared with a dealuminated zeolite Y faujasite molecular sieve (UOP, LZY-20M) having a bulk $Si_2O_3/Al_2O_3$ molar ratio of 11.4 (22.1 for tetrahedral framework alumina), which is bound and pelletized with 20 percent inert silica binder. The pellets are dried for 2 hr at 110° C. A 1 M aqueous solution of copper nitrate (5.0 g) is added to the dried pellets (5.0g) to impregnate the pellets with Cu(II) salt to incipient wetness. The impregnated pellets are thereafter dried in an oven under air at 110° C. for about 4 hr, and then calcined in air at 275° C. for several hr. The calcined pellets are hydrated in humid air to a water content of 8 percent, as determined by TGA. The hydrated composition (4.2 g) is loaded into a stainless steel tubular reactor (½ inch i.d.) with a concentric thermocouple well, and thereafter the ends of the reactor are packed with glass beads. A liquid feed comprising 40 mole percent butadiene in ethylbenzene is pumped into the reactor at a rate of 7 g/hr. The pressure of the reactor is maintained at 200 psig. A recycle pump is placed between the entrance and exit of the reactor to provide a recycle of 10/1. Deactivation of the catalyst is monitored.

At 100° C. the butadiene conversion is 50 mole percent, as measured by an on-line gas chromatograph. The conversion remains constant within 3 percent over a 200 hr test period. A 3 mole percent loss in conversion corresponds to a catalyst half-life ($\tau_{\frac{1}{2}}$) of 1000 hr, assuming pseudo-first order deactivation kinetics. The temperature of the reactor is raised to 115° C. The conversion increases to 60 mole percent and remains constant within 3 percent over a 180 hr test period, thereby corresponding to a $\tau_{\frac{1}{2}}$ of nearly 1000 hr. The results show that a copper impregnated faujasite zeolite catalyst reduced in situ in the dimerization reaction achieves a half-life of greater than 500 hr.

EXAMPLE 7

An impregnated catalyst is prepared as in Example 6, with the exception that the copper content is 7.5 percent (dry basis). The catalyst is hydrated to 8.5 percent water concentration. The catalyst (75 g) is placed in a stainless steel basket in a 1 l continuously stirred tank reactor. The reactor is heated to 100° C., and a feedstream comprising butadiene, n-butane, and ethylbenzene in a molar ratio of 1:1:0.5 is passed into the reactor at a feed rate of 160 g/hr and a pressure of 500 psig. The butadiene conversion, which remains essentially constant for the test time of 100 hr, is 43 mole percent, corresponding to a $\tau_{\frac{1}{2}}$ of greater than 500 hr. On conversion to a feedstream comprising butadiene and n-butane in a molar ratio of 1:1 for a test time of 150 hr, comparable results are obtained with a calculated $\tau_{\frac{1}{2}}$ of greater than 1000 hr. The half-life $\tau_{\frac{1}{2}}$ remains greater than 1000 hr on increasing the reaction temperature to 115° C. The results show that a copper impregnated faujasite zeolite catalyst reduced in situ in the dimerization reaction maintains excellent lifetime under different feedstreams and at different reaction temperatures.

EXAMPLE 8

An impregnated catalyst is prepared as in Example 6, with the exception that the inert silica binder content is 15 percent. The catalyst is employed in the dimerization of butadiene in the reactor and under the process conditions described in Example 6. The butadiene conversion is 48 mole percent, and there is no detected deactivation of the catalyst within the 100 hr test period. The catalyst is subjected to regeneration conditions comprising burning in air at 275° C. for several hours, followed by rehydration to 8 percent water concentration. The regenerated catalyst is re-run in the dimerization reaction for 100 hr. The used catalyst is regenerated and re-run in the dimerization reaction a second time. After a third regeneration the catalyst is re-run again in the dimerization reaction under the conditions of Example 6. The butadiene conversion is 49 mole percent with no deactivation during the test time of 240 hr. The calculated $\tau_{\frac{1}{2}}$ is greater than 1000 hr. The experiment shows that the copper-impregnated catalyst of this invention is easily regenerated and that oxidation and burn-off do not adversely affect the catalyst's performance.

EXAMPLE 9

An impregnated catalyst is prepared as in Example 6, with the exception that the binder is alumina (UOP) in a concentration of 20 percent. The catalyst is employed in the dimerization of butadiene as in Example 6. A conversion of 50 mole percent is obtained with essentially no deactivation over a 200 hr test period. The calculated $\tau_{\frac{1}{2}}$ is greater than 1000 hr. This experiment, taken with Experiments 6, 7, and 8, shows that different inert binders do not materially affect the catalyst's performance.

COMPARATIVE EXPERIMENT 1

An impregnated catalyst is prepared as in Example 6, with the exception that the LZ-20M sieve is replaced by a zeolite Y-54 sieve having a bulk $SiO_2/Al_2O_3$ molar ratio of 5/1 and a framework $SiO_2/Al_2O_3$ molar ratio of 5/1. The catalyst is tested in the dimerization of butadiene as in Example 6 using a feed mixture of butadiene (BD) and ethylbenzene (EB) in a BD:EB molar ratio of 1:1.5. The catalyst deactivates with a measured $\tau_{\frac{1}{2}}$ of 25 hr. When Comparative Example 1 is compared with Example 6, it is seen that the combination of low bulk and low framework $SiO_2/Al_2O_3$ molar ratios of the comparative catalyst is detrimental to the lifetime and stability of the catalyst.

EXAMPLE 10

A catalyst is prepared as in Example 6, with the exception that samples of the catalyst are hydrated as in Table V.

TABLE V

| Sample | Wt. % $H_2O$ | k (mole-hr)$^{-1}$ |
| --- | --- | --- |
| E-10-a | 2.0 | 0.21 |
| E-10-b | 3.6 | 0.21 |
| E-10-c | 6.5 | 0.31 |
| E-10-d | 10.5 | 0.25 |
| E-10-e | 14.2 | 0.23 |
| E-10-f | 3.4 | 0.27 |

Figure 3:
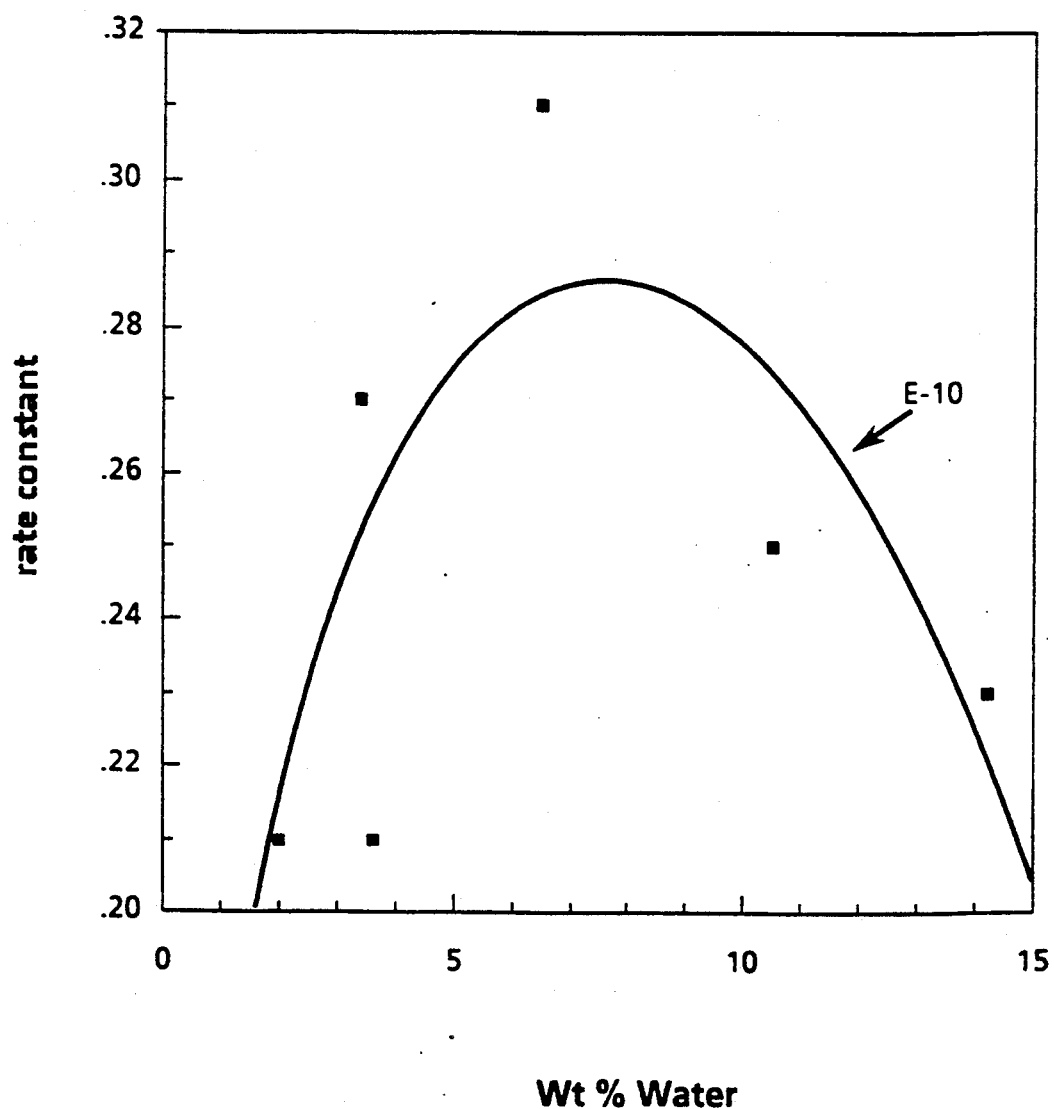

The catalyst sample (4 g) is placed in an annular basket in a 300 cc Parr reactor equipped with a stirrer and sampling tube. Butadiene (29 g) and ethylbenzene (100 cc) are added to the reactor under nitrogen at room temperature. The reactor temperature is raised to 100° C. at a total pressure of 440 psig. The reaction mixture is sampled at various times, and the second order rate constant for the formation of vinylcyclohexene is calculated from a plot of (butadiene concentration)$^{-1}$ versus time with the results shown in Table V and plotted in FIG. 3. It is seen that a maximum catalyst activity is achieved at a water concentration of about 7 to 8 percent.

EXAMPLE 11

Three impregnated catalysts are prepared as in Example 6, with the exception that the LZ-20M sieve is replaced by a SA-15AE sieve (UOP) having a bulk $SiO_2/Al_2O_3$ molar ratio of 37 and a framework $SiO_2/Al_2O_3$ molar ratio of 40, and with the exception that the water concentration is as follows: (a) 1.7 percent, (b) 5.6 percent, (c) 8.0 percent. The catalyst is tested in the dimerization of butadiene as in Example 10. The half-life of these catalysts is measured at greater than 1000 hr. At 115° C. the following rate constants for the formation of vinylcyclohexene are measured: (a) 0.053 (mole-hr)$^{-1}$: (b) 0.068 (mole-hr)$^{-1}$;(c) 0.069 (mole-hr)$^{-1}$. It is seen that the impregnated catalysts having bulk and framework $SiO_2/Al_2O_3$ molar ratios of about 40 achieve a long lifetime in the cyclodimerization process. Although the rate constants are observed to be low at 115° C., this process can be run at higher temperatures to achieve higher rate constants.

What is claimed is:

1. A process for the cyclodimerization of 1,3-butadiene or substituted 1,3-butadiene to 4-vinylcyclcohexene or a substituted derivative thereof, the process comprising contacting 1,3-butadiene or a substituted 1,3-butadiene with a catalytic amount of a catalyst composition containing copper(I) ions supported on a carrier and containing a promoting amount of an hydroxylic solvent such that the promoting amount of hydroxylic solvent ranges from about 2.5 to about 22 weight percent when the catalyst is prepared by ionexchanging copper ions into the carrier, or alternatively, such that the promoting amount of hydroxylic solvent ranges from abut 3 to about 14 weight percent when the catalyst is prepared by impregnating copper ions onto the carrier, the contacting of the 1,3-butadiene or substituted 1,3-butadiene with the catalyst occurring under reaction conditions such that the activity of the catalyst, a measured by the rate of formation of 4-vinylcyclohexene or substituted 4-vinylcyclohexene, is increased when compared with a control process which is identical to the process of this invention with the exception that the control catalyst contains no greater than 2 weight percent of an hydroxylic solvent.

2. The process of claim 1 wherein 1,3-butadiene is employed.

3. The process of claim 1 wherein the substituted butadiene is isoprene or chloroprene.

4. The process of claim 1 wherein a diluent is employed.

5. The process of claim 1 wherein the diluent is ethylbenzene.

6. The process of claim 1 wherein the concentration of 1,3-butadiene or substituted 1,3-butadiene in the feedstream ranges from about 10 to about 80 volume percent.

7. The process of claim 1 wherein the carrier is selected from the group consisting of crystalline aluminosilicate zeolites, non-zeolitic silica-alumina mixtures, silica, silica gels, alumina, and montmorillonite clays.

8. The process of claim 7 wherein the carrier is an aluminosilicate zeolite.

9. The process of claim 8 wherein the carrier is a faujasite zeolite.

10. The process of claim 1 wherein a binder is employed in the carrier.

11. The process of claim 9 wherein the catalyst is prepared by ion-exchange.

12. The process of claim 11 wherein the ion-exchanged catalyst contains Group IIA metal ions.

13. The process of claim 12 wherein the ion-exchanged catalyst contains calcium.

14. The process of claim 11 wherein the ion-exchanged catalyst is pre-reduced with a reducing agent selected from the group consisting of ammonia, carbon monoxide, hydrogen, and hydrazine.

15. The process of claim 14 wherein the reducing agent is ammonia.

16. The process of claim 15 wherein the hydroxylic solvent is water in a concentration in the range from about 4 to about 14 weight percent.

17. The process of claim 14 wherein the reducing agent is hydrazine in the presence of base.

18. The process of claim 17 wherein the hydroxylating solvent is water in a concentration in the range from about 10 to about 21 weight percent.

19. The process of claim 9 wherein the catalyst is prepared by impregnation.

20. The process of claim 19 wherein the catalyst is prepared by impregnation to incipient 21. The process of claim 20 wherein the impregnated catalyst is reduced in situ-n the dimerization 22. The process of claim 19 wherein the bulk $SiO_2/Al_2O_3$ molar ratio is in the range from about 5 to about 50.

23. The process of claim 20 wherein the hydroxylating solvent is water in a concentration in the range from about 4 to about 12 weight percent.

24. The process of claim 19 wherein the catalyst exhibits a half-life of at least about 500

25. The process of claim 19 wherein the catalyst exhibits a half-life of at least about 1000 hr.

26. The process of claim 1 wherein the catalyst is hydroxylated by exposure to a moist atmosphere.

27. The process of claim 1 wherein the process temperature is in the range from about 70° C. to about 170° C.

28. The process of claim 1 wherein the process pressure is in the range from about 100 psig to about 1000 psig.

29. The process of claim 1 wherein the weight hourly space velocity is in the range from about 0.01 $hr^{-1}$ to about 100 $hr^{-1}$.

30. The process of claim 1 wherein the increase in rate constant for the formation of vinylcyclohexene ranges from about 25 to about 500 percent.

31. The process of claim 1 wherein the catalyst is regenerated by a an oxygen burn-off, followed by treatment with a hydroxylic solvent.

32. The process of claim 1 wherein the reactants and products are maintained in the liquid phase.

33. A process of dimerizing 1,3-butadiene to 4-vinylcyclohexene comprising contacting 1,3-butadiene with a catalytic amount of a catalyst comprising a copper(I)-impregnated faujasite zeolite containing water in a concentration ranging from about 4 to about 12 weight percent, the contacting occurring at a temperature in the range from about 80° C. to about 130° C. and a pressure in the range from about 300 psig to about 700 psig such that 4-vinylcyclohexene is formed in a conversion of at least about 30 mole percent, a selectivity of at least about 97 mole percent, and such that the rate constant for the formation of vinylcyclohexene is increased over a similar process wherein the water concentration is no greater than about 2 percent.

34. A process for the cyclodimerization of 1,3-butadiene or substituted 1,3-butadiene to 4-vinylcyclohexene or a substituted derivative thereof, the process comprising contacting 1,3-butadiene or a substituted 1,3-butadiene with a catalytic amount of a copper(I)-impregnated aluminosilicate zeolite wherein the zeolite is selected from the group consisting of faujasites, mordenite, zeolite L, zeolite $\Omega$, and Zeolite beta, the contacting occurring under reaction conditions such that vinylcyclohexene is formed in high selectivity and the half-life of the catalyst is at least about 500 hours.

35. The process of claim 34 wherein 1,3-butadiene is employed.

36. The process of claim 34 wherein a diluent is employed.

37. The process of claim 34 wherein the concentration of 1,3-butadiene or substituted 1,3-butadiene in the feedstream ranges from about 10 to about 80 volume percent.

38. The process of claim 34 wherein a binder is employed with the catalyst.

39. The process of claim 38 wherein the binder is alumina.

40. The process of claim 34 wherein the zeolite is a faujasite.

41. The process of claim 40 wherein the bulk $SiO_2/Al_2O_3$ molar ratio of the zeolite is in the range from about 5 to about 50 and the framework $SiO_2/Al_2O_3$ molar ratio is at least about 15.

42. The process of claim 41 wherein the bulk $SiO_2/Al_2O_3$ molar ratio of the zeolite is in the range from about 10 to about 45 and the framework $SiO_2/Al_2O_3$ molar ratio is at least about 22.

43. The process of claim 34 wherein the catalyst exhibits a half-life of at least about 1000 hours.

44. The process of claim 34 wherein the process temperature is in the range from about 70° C. to about 150° C.

45. The process of claim 34 wherein the process pressure is in the range from about 100 psig to about 1000 psig.

46. The process of claim 34 wherein the weight hourly space velocity is in the range from about 0.01 $hr^{-1}$ to about 100 $hr^{-1}$.

47. The process of claim 34 wherein the catalyst is regenerated by an oxygen burn-off, followed by treatment with a hydroxylic solvent.

48. The process of claim 34 wherein the reactants and products are maintained in the liquid state.

49. The process of claim 34 wherein the selectivity is at least about 95 mole percent.

50. The process of claim 34 wherein the selectivity is at least about 99 mole percent.

51. The process of claim 34 wherein the zeolite is mordenite.

52. The process of claim 34 wherein the zeolite is zeolite L.

53. The process of claim 34 wherein the zeolite is zeolite beta.

54. The process of claim 34 wherein the zeolite is zeolite $\Omega$.

55. The process of claim 1 wherein the hydroxylic solvent is water.

* * * * *

UNITED STATES PATENT AND TRADEMARK OFFICE
CERTIFICATE OF CORRECTION

PATENT NO. : 5,196,621

DATED : March 23, 1993

INVENTOR(S) : Ronald W. Diesen; Kenneth A. Burdett; Ravi S. Dixit; Stanley S. T. King and Michael M. Olken It is certified that error appears in the above-identified patent and that said Letters Patent is hereby corrected as shown below:

In Claim 1, Column 18, line 20, "the catalyst is prepared by ionexchanging" should correctly read --the catalyst is prepared by ion-exchanging--.

In Claim 1, Column 18, line 28, "a measured by the rate of formation" should correctly read --as measured by the rate of formation--.

In Claim 20, Column 19, line 12, "impregnation to incipient" should correctly read --impregnation to incipient wetness--.

In Claim 21, Column 19, line 14, "catalyst is reduced in situ-n the dimerization" should correctly read --catalyst is reduced in situ in the dimerization process--.

In Claim 24, Column 19, line 22, "a half-life of at least about 500" should correctly read --a half-life of at least about 500 hours--.

Signed and Sealed this

First Day of February, 1994

Attest:

BRUCE LEHMAN

Attesting Officer

Commissioner of Patents and Trademarks